United States Patent [19]

Delang

[11] Patent Number: 4,512,466
[45] Date of Patent: Apr. 23, 1985

[54] SURGICAL INSTRUMENT ORGANIZER

[76] Inventor: Theodore G. Delang, 3440 N. Lake Shore Dr., Apt. 11G, Chicago, Ill. 60657

[21] Appl. No.: 628,022

[22] Filed: Jul. 5, 1984

[51] Int. Cl.³ ............................................. B65D 85/62
[52] U.S. Cl. .................................. 206/370; 206/372; 206/493; 206/482; 211/70.6
[58] Field of Search ............... 206/370, 372, 482, 493, 206/449, 565, 478; 211/70.6

[56] References Cited

U.S. PATENT DOCUMENTS

| | | | |
|---|---|---|---|
| 1,718,996 | 7/1929 | Blocker | 211/70.6 |
| 3,925,014 | 12/1975 | Langdon | 206/370 |
| 4,043,754 | 8/1977 | Sklar | 206/565 |
| 4,135,868 | 1/1979 | Schainholz | 211/70.6 |
| 4,142,632 | 3/1979 | Sandel | 206/478 |
| 4,229,420 | 10/1980 | Smith et al. | 206/370 |
| 4,262,799 | 4/1981 | Perrett | 206/493 |
| 4,342,391 | 8/1982 | Schainholz | 206/370 |
| 4,465,186 | 8/1984 | Meyers | 206/493 |

Primary Examiner—William T. Dixson, Jr.
Attorney, Agent, or Firm—Gary, Juettner & Pyle

[57] ABSTRACT

A surgical instrument organizer for receiving a plurality of stacked instruments of the hinged type and for holding the instruments open, is characterized by a base, a pair of finger ring posts extending upwardly from the base for extension through respective finger rings of the instruments, a shaft separator extending upwardly from the base and between the shafts of the instruments and a tip separator also extending upwardly from the base and between jaws of the instrument. Upper ends of the finger ring posts and shaft separator may be fastened together to retain the instruments on the organizer and maintain the instruments, along with the tip separator, in an open condition. The organizer advantageously supports the instruments during sterilization thereof, with complete sterilization being assured since the instruments are held open, and a forward end and sides of the base extend outwardly of the instrument tips to protect the same against contact and damage. After sterilization, the instruments may conveniently be carried on the organizer to an operating theater and removed therefrom as required. Preferably, the organizer is of an economical material such as cardboard and may be reused a number of times, although it may also be economically discarded after a single use.

14 Claims, 5 Drawing Figures

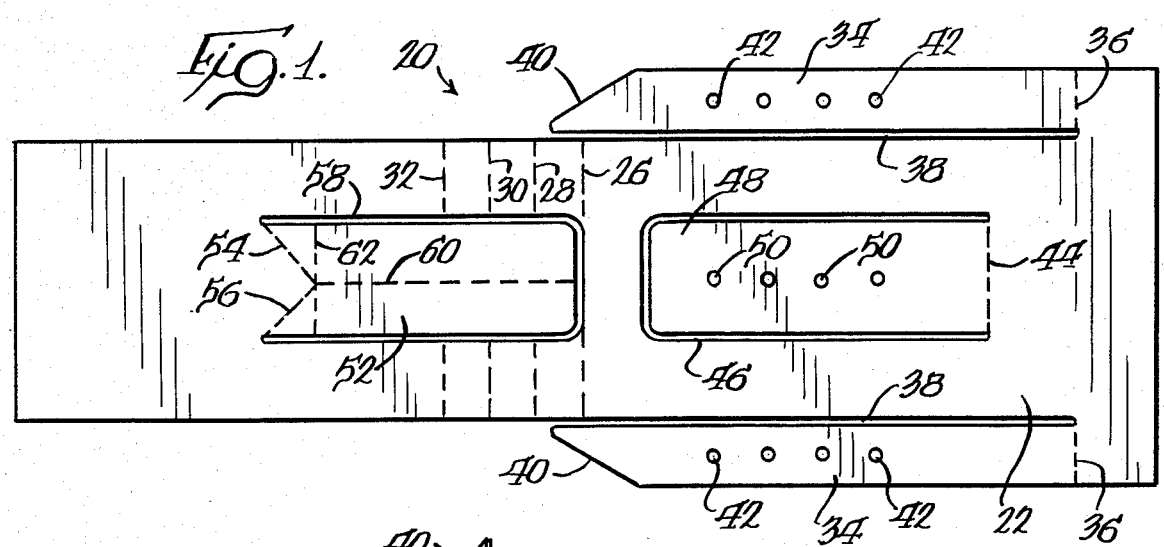
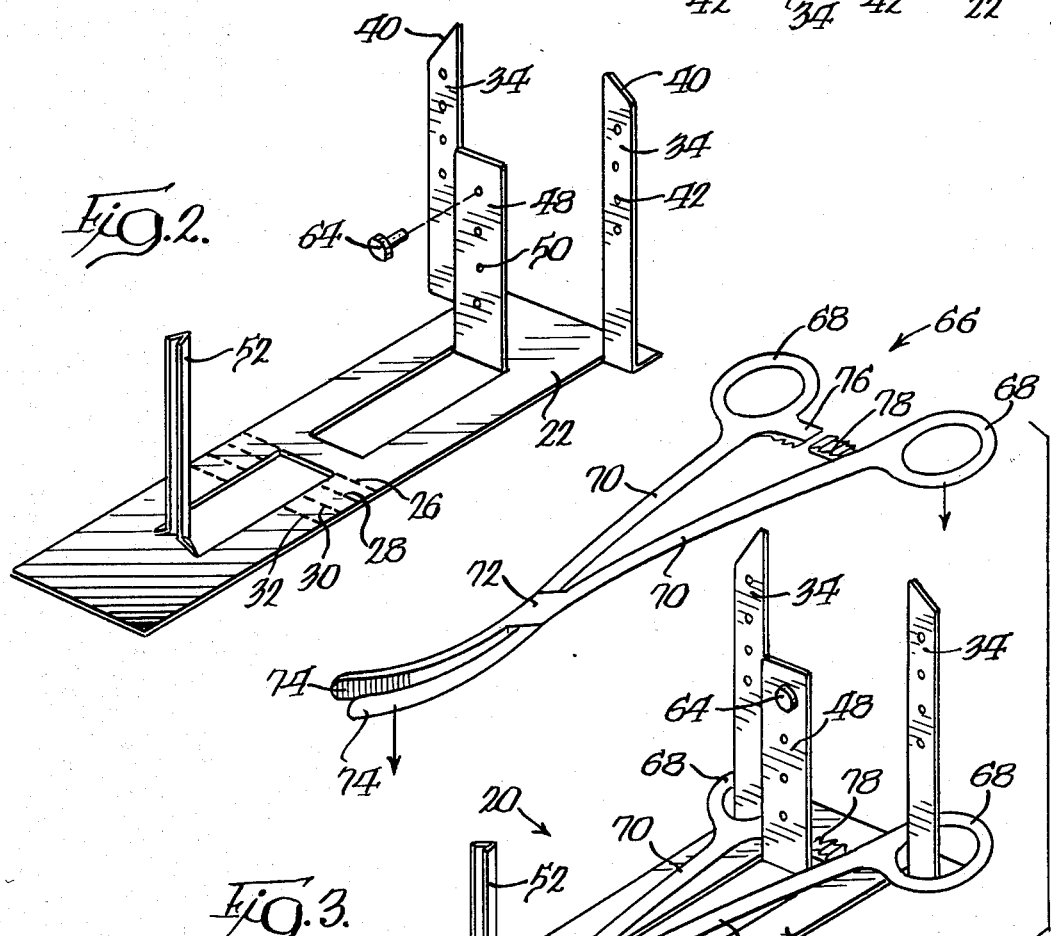
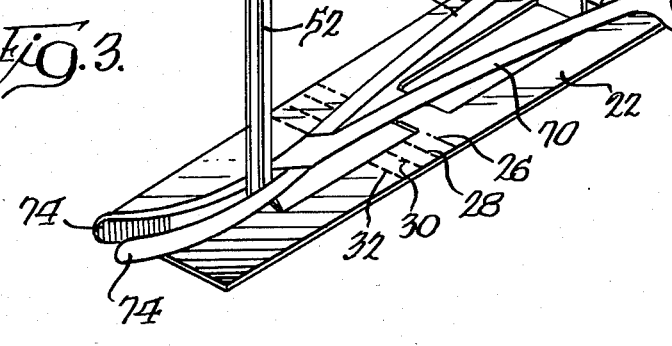

U.S. Patent Apr. 23, 1985 Sheet 2 of 2 4,512,466
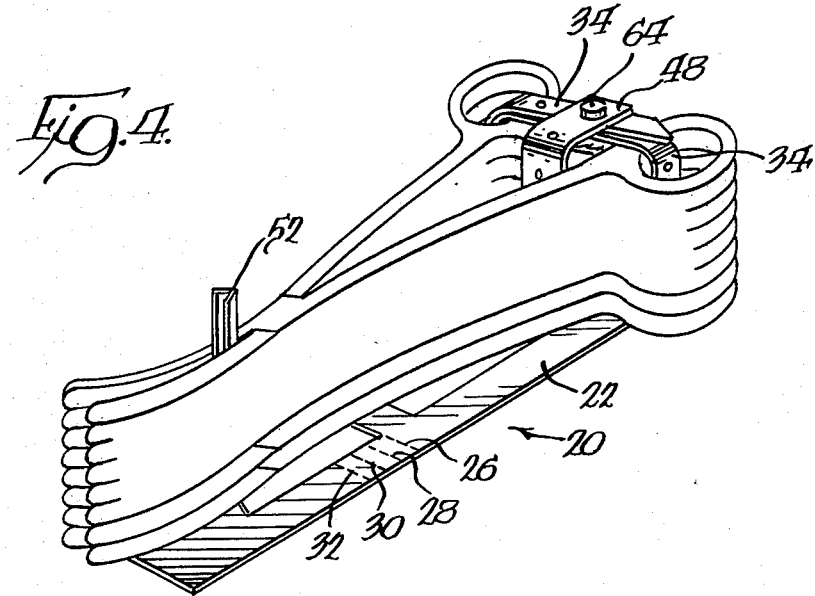
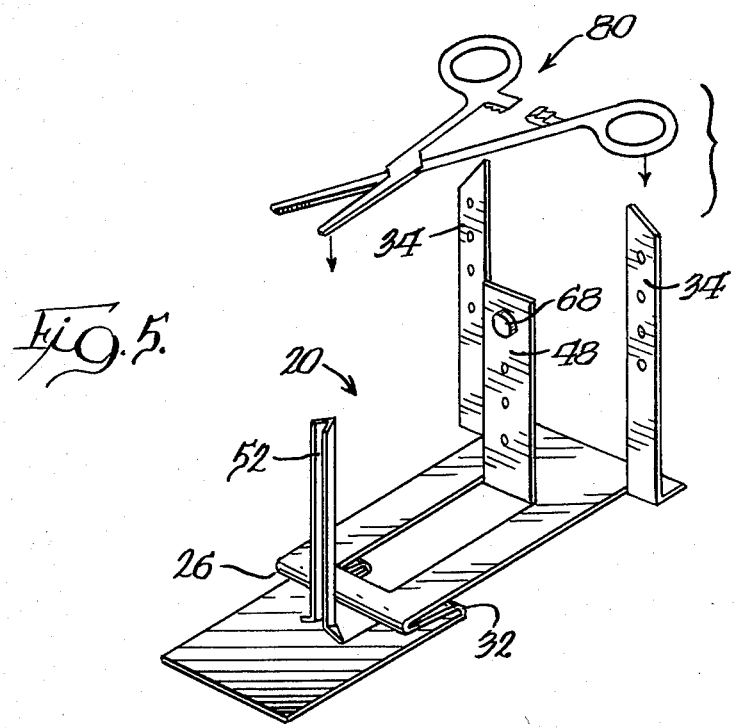

SURGICAL INSTRUMENT ORGANIZER

BACKGROUND OF THE INVENTION

The present invention relates to an instrument organizer, and in particular to a surgical instrument organizer which is formed of an economical material such as cardboard and which maintains a plurality of instruments stacked thereon in an open condition.

It is well known that surgical instruments must be sterilized, usually by exposure to saturated steam, prior to being used in a surgical procedure. A plurality of instruments are sterilized simultaneously, and although mere contact between the instruments is not a problem, should an instrument of the hinged type accidentally be locked closed during sterilization, the steam will not be able to contact the areas of the instrument which are brought together under pressure, possibly resulting in the instrument not being completely sterilized.

With the foregoing in mind, efforts are made to keep the instruments of the hinged type open during sterilization. According to one procedure, a wire ring for holding instruments during sterilization is opened and fed through one of the finger ring posts of each of a plurality of instruments, thus holding the instruments together. The instruments are opened when placed on the ring, but because they may be jossled incident to placing a quantity of instruments into a sterilizing tray, as well as during transport of the tray into a sterilizer, it often happens that one or more closes and locks.

A large number of instruments of various types are sterilized in the container, and after sterilization are transported to an operating theater and manually arranged according to type, so that they will be readily available during the surgical procedure. Because the instruments are spread out in the sterilizing tray, often one on top of and occasionally interlocked with the other, arranging the instruments in this manner is time intensive and inefficient.

Another known technique for sterilizing such instruments contemplates using a tray having a mesh bottom and pins or posts extending up from the bottom for extending through the finger rings of the instruments to maintain them open during sterilization. However, after sterilization the above described manual arrangement of the instruments in the operating theater is still required.

OBJECTS OF THE INVENTION

An object of the present invention is to provide a surgical instrument organizer for holding and maintaining open a plurality of instruments stacked thereon during sterilization of the instruments, thereby to ensure that all of the instruments are properly sterilized, organized and remain undamaged.

Another object is to provide such an organizer which, after sterilization of the instruments, may be used to transport the instruments to an operating theater for dispensing of the instruments directly therefrom during a surgical procedure.

A further object is to provide such an organizer which is economically formed of cardboard and may be folded to various configurations to accommodate different sizes of surgical instruments.

SUMMARY OF THE INVENTION

In accordance with the present invention, an organizer for instruments of the type having a pair of finger rings each connected by an associated shaft to an associated jaw through a hinged connection for closing and opening the jaws in response to respective movement of the finger rings toward and away from each other, comprises a base; a pair of elongate finger ring posts extending upwardly from opposite sides of said base toward one end thereof; an elongate jaw separator extending upwardly from said base toward an opposite end thereof from a position generally intermediate said base sides; and an elongate shaft divider extending upwardly from said base intermediate said finger ring posts and jaw separator from a position generally intermediate said base sides. Said organizer accommodates placement of the instrument thereon, such that said finger ring posts extend upwardly through assocaited ones of the instrument finger rings, said jaw separator extends upwardly between open jaws of the instrument and said shaft divider extends upwardly between the instrument shafts. In this manner, said organizer supports the instrument thereon and prevents the instrument from going from an open to a closed position whereat the finger rings move together and the jaws close.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 is a top plan view of a cardboard cutout which may be folded to define a surgical instrument organizer in accordance with the teachings of the present invention;

FIG. 2 is a perspective view of the instrument organizer, showing the same folded in a manner to receive instruments and to maintain the instruments open;

FIG. 3 shows surgical instruments of one size received on and maintained open by the organizer;

FIG. 4 illustrates portions of the organizer fastened together to secure a plurality of instruments on the organizer in open condition; and FIG. 5 illustrates further folding of the instrument organizer to accommodate instruments of a smaller size.

DETAILED DESCRIPTION

Referring to the drawings, there is indicated generally at 20 a surgical instrument organizer which is adapted to receive and support a plurality of hinged instruments in a stack while maintaining the instruments open. Then instrument organizer is preferably of an economical but foldable material such as cardboard so that, as seen in FIG. 1, it may initially be manufactured as a flat, die cut piece from a sheet of the material, whereby a plurality of the flat pieces may be stacked one on top of the other to facilitate transport and storage of the same.

With particular reference to FIG. 1, as initially manufactured the instrument organizer 20 is planar and includes a base 22 having a plurality of creased fold lines 26, 28, 30 and 32 spaced longitudinally therealong and extending transversely thereacross. A pair of finger ring posts 34 extend along opposite sides of a rearward portion of the base and connect at rearward ends thereof to the base along fold lines 36. The finger ring posts are separated along inner sides thereof from the base by slots 38, and each has a tapered free end 40 and a plurality of longitudinally spaced openings 42. Also connected to the rearward portion of the base along a fold line 44, but otherwise separated therefrom by a generally U-shaped slot 46, is a shaft divider 48 having a plurality of longitudinally spaced openings 50.

The forward portion of the base 22 carries a tip separater 52 connected to the base along a pair of fold lines 54 and 56, but otherwise separated therefrom by a generally U-shaped slot 58. The fold lines extend toward each other from opposite ends of the slot and meet to form a "V", and a fold line 60 extends longitudinally along the tip separator from the juncture of the fold lines 54 and 56. In addition, a fold line 62 extends transversely of the tip separator through the juncture of the fold lines 54, 56 and 60.

FIG. 2 illustrates the instrument organizer 20 folded to a configuration for receiving a stack of hinged surgical instruments. To go from the configuration of FIG. 1 to that of FIG. 2, the finger ring posts 34 are folded about the fold lines 36, and the shaft divider 48 about the fold line 44, to extend the same vertically upwardly from the base 22. The tip separator 52 is, in turn, folded along the fold line 60 and simultaneously along the fold lines 54, 56 and 62 to extend it vertically upwardly from the base, thereby to form the organizer to the configuration shown in FIG. 2. At this point it may be noted that the organizer also includes a latch pin 64, which after die cutting of the organizer is extended though one of the shaft divider openings 50 for being retained in the opening until such time as it is used for a purpose to be described.

As folded, the instrument organizer 20 is configured to receive surgical instruments, such as the instrument indicated generally at 66 in FIG. 3, and to support the instruments in a stack while holding the same open. The instrument 66 includes a pair of finger rings 86 connected through associated shafts 70 and a hinged connection or box lock 72 with a pair of jaws 74 comprising a working end or tip of the instrument. Extending toward each other from opposite ones of the finger rings are ratchets 76 and 78, which when the finger rings are moved closely together intermesh to lock the instrument closed with the jaws 74 then being firmly engaged one against the other.

As previously mentioned, during sterilization mere contact between instruments is not detrimental to the sterilization process, but a pressure contact between surfaces of the instruments may result in the process being incomplete. Thus, if the ratchets 76 and 78 were to accidentally become locked during sterilization, the contacting surface areas of the ratchets and jaws would be urged together with sufficient pressure to possibly prevent sterilization of those areas. Accordingly, one purpose of the instrument organizer 20 is to ensure that during sterilization the ratchets do not and cannot become locked, and the jaws 74 do not and cannot be moved together.

To that end, the surgical instrument 66 is placed on the organizer 20 in such manner that the finger ring posts 34 extend through respective ones of the finger rings 68, the shaft divider 48 extends between the shafts 70 forwardly of the ratchets 76 and 78, and the tip separator 52 extends between the open instrument jaws 74. As is apparent, the finger ring posts and the shaft divider prevent any accidental movement of the finger rings and shafts toward each other, while at the same time the tip separator prevents movement together of the jaws and, along with the finger ring posts and shaft divider, aids in securing the instrument on the organizer and preventing lateral movement of the instrument on the organizer. Consequently, the organizer obviates the possibility of the instrument accidentally being locked closed.

FIG. 4 illustrates a plurality of the instruments 66 stacked on the organizer 20, and when so stacked they are secured in place by means of folding the finger ring posts 34 toward and across one another and the shaft divider 48 across the finger ring posts, and by then extending the latch pin 64 through aligned openings in the shaft divider and finger rings posts. With the plurality of instruments so fastened in place, sterilization of the instruments while on the organizer may then be effected without danger of the instruments closing or locking during the process. Although the organizer may be of cardboard, since steam used for sterilization is saturated, not wet, the integrity and strength of the organizer is not adversely affected by the steam. After sterilization is complete, the instruments may then be transported on the organizer to an operating theater and dispensed directly therefrom during a surgical procedure simply by removing the latch pin 64. Consequently, in addition to ensuring proper sterilization of the instruments, as compared with the prior technique of manually arranging the instruments on trays in an operating theater, the organizer 20 provides an improved means for maintaining and supporting the instrument in a readily accessible condition.

FIG. 5 illustrates the manner in which the instrument organizer 20 may be further folded to accommodate receipt and support in open condition of a stack of smaller and shorter surgical instruments, such as an instrument indicated generally at 80, which except for its size and length is similar to the instrument 66. If the instrument 80 were placed on the organizer with the organizer in its configuration shown in FIG. 2, although the finger ring posts 34 would extend through the instrument finger rings and the shaft divider 48 between the instrument shafts forwardly of the ratchets, because of the shorter length of the instrument, the jaws would not reach the tip separator 52. Therefore, to bring the tip separator closer to the finger ring posts and shaft divider, so that the tip separator will then extend between the jaws of the instrument 80, for the size of the instrument shown the base 22 is folded back and forth upon itself along the fold lines 26 and 32. It is understood, of course, that if an instrument of a length intermediate those of the instruments 66 and 80 were to be accommodated, then the base would be folded back and forth upon itself along the fold line 26 and an appropriate one of the lines 28 and 30.

The invention thus provides an instrument organizer for supporting a plurality of stacked surgical instruments while maintaining the same in an open, unlocked condition, both during sterilization and in an operating theater for convenient dispensing of the instruments from the organizer. Although the organizer has been described as being of cardboard, it may be of any other suitable material, it being appreciated that use of a foldable material such as cardboard advantageously permits economical manufacture of the organizer simply by die cutting the same from a sheet of the material, as well as convenient storage of a plurality of the organizers in a stack. However, the invention is not limited to manufacturing the organizer from a foldable material, and it could just as readily be manufactured of another material to the configuration shown in FIG. 2, for example a material such as plastic or metal.

While embodiments of the invention have been described in detail, various modifications and other embodiments thereof may be devised by one skilled in the art without departing from the spirit and scope of the invention, as defined in the appended claims.

What is claimed is:

1. An organizer for instruments of the type having a pair of finger rings each connected by an associated shaft to an associated jaw through a hinged connection for closing and opening the jaws in response to respective movement of the finger rings toward and away from each other, said organizer comprising a base; a pair of elongate finger ring posts extending upwardly from opposite sides of said base toward one end thereof; an elongate jaw separator extending upwardly from said base toward an opposite end thereof from a position generally intermediate said base sides; and an elongate shaft divider extending upwardly from said base intermediate said finger ring posts and jaw separator from a position generally intermediate said base sides, said organizer accommodating placement of the instrument thereon, such that said finger ring posts extend upwardly through associated ones of the instrument finger rings, said jaw separator extends upwardly between open jaws of the instrument and said shaft divider extends upwardly between the instrument shafts, whereby said organizer supports the instrument thereon and prevents the instrument from going from an open to a closed position whereat the finger rings move together and the jaws close.

2. An organizer as in claim 2, wherein said organizer accommodates placement of a plurality of instruments thereon in a stack, and including means for fastening together upper ends of at least two of said finger ring posts and shaft divider to secure the instruments on said organizer.

3. An organizer as in claim 2, wherein said means for fastening includes means for fastening together upper ends of all of said finger ring posts and shaft divider.

4. An organizer as in claim 3, wherein said upper ends of said finger ring posts and shaft divider each have an opening therethrough and the same are foldable in overlapping relationship to align said openings, said means for fastening also including a pin extendable through said aligned openings to fasten said finger ring posts and shaft divider in said overlapping relationship.

5. An organizer as in claim 1, including means for varying the effective length of said base between said jaw separator and shaft divider to adjust the distance between said jaw separator and each of said finger ring posts and shaft divider, whereby said organizer may be adjusted to receive thereon instruments of different lengths.

6. An organizer as in claim 5, wherein said means for varying includes said base being of a foldable material and said base is folded back and forth upon itself between said jaw separator and said shaft divider to move said jaw separator closer to each of said shaft divider and finger ring posts.

7. An organizer for surgical instruments of the type having a pair of finger rings each connected by an associated shaft to an associated jaw of a tip of the instrument through a hinged connection for opening and closing the jaws in response to respective movement of the finger rings toward and away from each other, said organizer comprising a generally planar sheet of a foldable material which includes an elongate base; a pair of elongate finger ring posts extending longitudinally along opposite sides of said base, connected at one end with said base toward one end of said base and separated from said base along inner longitudinal sides thereof; an elongate shaft divider extending longitudinally along said base generally medially thereof and between said finger ring posts, connected at one end with said base further from said base one end than said point of connection between said base and said finger ring posts and separated from said base around the remainder of its periphery; and an elongate jaw separator extending longitudinally along said base generally medially thereof toward an opposite end of said base with respect to said shaft divider, connected at one end thereof with said base and separated from said base around the remainder of its periphery, each of said finger ring posts, shaft divider and jaw separator being foldable at the points of connection of the same with said base to extend the same upwardly from said base, whereby said organizer accommodates placement of the surgical instrument thereon, such that said finger ring posts extend upwardly through associated ones of the instrument finger rings, said jaw separator extends upwardly between open jaws of the surgical instrument and said shaft divider extends upwardly between the surgical instrument shafts, whereby said organizer supports the surgical instrument thereon and prevents the instrument from going from an open to a closed position whereat the finger rings move together and the jaws close, so that when said organizer supports the surgical instrument during sterilization thereof, the instrument is held continuously open for complete sterilization.

8. An organizer as in claim 7, including fold lines along the points of connection between said base and each of said finger ring posts, shaft divider and jaw separator to facilitate folding of the same with respect to said base.

9. An organizer as in claim 7, wherein said sheet of foldable material is cardboard.

10. An organizer as in claim 7, wherein said organizer accommodates placement of a plurality of surgical instruments thereon in a stack, and including means for fastening together upper ends of at least two of said finger ring posts and shaft divider to secure the surgical instruments on said organizer.

11. An organizer as in claim 10, wherein said means for fastening includes means for fastening together upper ends of all of said finger ring posts and shaft divider.

12. An organizer as in claim 11, wherein said upper ends of said finger ring posts and shaft divider each have an opening therethrough and the same are foldable in overlapping relationship to align said openings, said means for fastening also including a pin extendable through said aligned openings to fasten said finger ring posts and shaft divider in said overlapping relationship.

13. An organizer as in claim 7, including means for varying the effective length of said base between said jaw separator and shaft divider to adjust the distance between said jaw separator and each of said finger ring posts and shaft divider, whereby said organizer may be adjusted to receive thereon instruments of different lengths.

14. An organizer as in claim 13, wherein said means for varying includes a plurality of fold lines on said base spaced longitudinally therealong and extending transversely thereof intermediate said points of connection of said shaft divider and jaw separator with said base, said fold lines facilitating folding of said base back and forth upon itself along a selected two of said fold lines to move said jaw separator a selected distance closer to each of said shaft divider and finger ring posts.

* * * * *